United States Patent [19]

Rague et al.

[11] Patent Number: 4,851,694
[45] Date of Patent: Jul. 25, 1989

[54] DEVICE FOR DRIVING AND POSITIONING A SOURCE HOLDER IN AN APPLICATOR USED IN RADIOTHERAPY

[75] Inventors: Bruno Rague, Bures sur Yvette; André Olombel, Briis sous Forges, both of France

[73] Assignee: Campaignie ORIS Industrie, Paris, France

[21] Appl. No.: 149,015

[22] Filed: Jan. 27, 1988

[30] Foreign Application Priority Data

Jan. 28, 1987 [FR] France ............................. 87 00992

[51] Int. Cl.⁴ .............................................. G21F 5/02
[52] U.S. Cl. .............................. 250/497.1; 250/496.1
[58] Field of Search ................ 250/496.1, 497.1, 498.1

[56] References Cited

U.S. PATENT DOCUMENTS 3,669,093  6/1972  Sauerwein et al. ................ 128/1.1
3,861,380  1/1975  Chassagne et al. ............. 250/497.1
4,574,196  3/1986  Kampf .............................. 250/497.1

FOREIGN PATENT DOCUMENTS

0158630  3/1987  European Pat. Off. .
0189148  3/1987  European Pat. Off. .
2474374  7/1981  France .

Primary Examiner—Bruce C. Anderson

[57] ABSTRACT

The present invention relates to a device used for introducing one or more radioactive sources into an applicator (14) used in radiotherapy and positioning them there. The sources are mounted at one of a cable (40) of small diameter which is movable along a guide tube (38), one end of which communicates with the applicator. The cable (40) is driven by a motor-driven roller (48) which is capable of sliding on the cable (40). An encoder is equipped with a roller (52) which is in tangential contact, without sliding, with the cable (40). If the cable encounters an obstacle, the encoder roller (52) immediately ceases to rotate, and the encoder sends a signal to a programmable control unit (75). The invention relates to the transfer of radioactive sources in radiotherapy.

8 Claims, 5 Drawing Sheets

DEVICE FOR DRIVING AND POSITIONING A SOURCE HOLDER IN AN APPLICATOR USED IN RADIOTHERAPY

FIELD OF THE INVENTION

The present invention relates to the field of radiotherapy, and more particularly to a device with which a source holder can be introduced into and positioned in an applicator tube.

BACKGROUND OF THE INVENTION

In treating certain diseases such as breast cancers, it is known to introduce one or more tubes of small diameter, known as "applicator tubes" or "applicators", into the diseased organ, one or more radioactive sources being introduced into these applicators and allowed to act for a variable duration, generally on the order of one to two days. Most often, there are about 20 applicators involved, the number typically being between 5 and 30. The elements most recently used as the sources are iridium, cobalt, cesium and californium. These sources can be contained inside a tube called a "source holder", and it is this source holder that is introduced into the applicator. The sources may be in the form of grains, each of them several millimeters in length, or in the form of filaments of greater length. Hence the source holder may contain either a single filament or a plurality of grains disposed one after another, and separated from one another by spacers. The active length, that is, the length occupied by the sources, is equal to 150 mm at most. The source holder is mounted in the anterior portion of a movable cable along a guide tube that terminates in the applicator.

The problems that arise are not only that of driving the cable between an initial or storage position, in which the source holder is for instance inside a block of lead, to a final position or treatment position, in which the source holder is located inside the applicator, but also the problem of positioning the source holder, because it must be located at a very precise region inside the applicator, as well as the problem of detection of obstacles. It is essential that any obstacle encountered by the cable be detected, before it reaches its final position, and that the site of this obstacle be determined so that rapid intervention is possible.

Several solutions have been proposed so far. French Pat. No. 2 033 653 describes a device used especially in plesioradiotherapy, in which the source holder tube is driven by a metal cable. Controlling the position of the posterior end of this cable, that is, the end opposite that carrying the sources, is done with the aid of two end-of-course detectors, which detect the passage of this end. There is no provision for detection of obstacles in this device, and hence the cable is in danger of being blocked before its posterior end has passed the end-of-course detector corresponding to the final position, and thus it can happen that the sources are not located inside the applicator.

French Pat. No. 2 536 531 relates to a method of controlling the positioning of a source holder in a device of this generic type. Control is accomplished by analysis of the induced current of the motor driving the cable; the presence of an obstacle over the course causes the induced current of the motor to change, which enables the detection of the presence of this obstacle. A variation in the intensity of the current represents an increase in the load moment, and detecting this variation makes it possible to define a displacement time of the cable on which the source holder is mounted. This displacement time is compared with a reference time, which enables determining whether the cable is occupying an extreme position along its course, or is in an intermediate position. Although the presence of an obstacle can be detected with such a method, the exact position of the obstacle cannot be determined, because a certain amount of slippage, or sliding, can take place between the tube and the roller of the driving motor, and the exact length of the cable that has unwound is not known. For the same reason, it is no longer known with certainty that when the cable is in its final position, the source holder is indeed in its position inside the applicator.

European Pat. No. 0 152 124 also describes a device for driving and positioning a source holder in an applicator used in radiotherapy. In this device, the source holder is actuated via a metal cable, and the end of the cable opposite the sources is wound in a spiral over a groove provided on one face of a wheel driven by a rack. Positioning of the source holder in the applicator is done with the aid of a pneumatic system. Compressed air is sent through an opening located at one end of the guide tube, in which the cable moves, and the air exits by an opening located at the end of the guide tube closest to the applicator. The cable has a head that comes into contact with a stop when the source holder is in its place in the applicator, which prevents the air from leaving. A monitoring apparatus detects the resultant increase in pressure inside the tube sheath and stops the driving of the cable. There is no provision for an obstacle detection system in this device. As a result, if the cable is stopped by an obstacle prior to reaching its final position, the air will continue to exit via the second opening in the guide tube, and the cable will continue to unwind. It is therefore impossible to know whether there is an obstacle, or to detect the position of such an obstacle.

SUMMARY OF THE INVENTION

It is the object of the invention to overcome these disadvantages by providing a device for driving and positioning a source holder in an applicator used in radiotherapy with which the source holder cannot only be easily displaced but also positioned very precisely in the applicator, and with which an obstacle can be rapidly detected and the site of the obstacle can be determined easily and precisely.

More precisely, the subject of the present invention is a device for driving and positioning at least one source holder in an applicator tube used in radiotherapy, the applicator tube having a first end and a second end, the second end being open, the device comprising the following:

a guide tube having one end capable of being connected to the second end of the applicator, a cable adapted to be displaced longitudinally along the guide tube and the applicator between a first position and a second position, the cable having a first end in the vicinity of which the source holder can be mounted, and a second end, and means for driving the cable along the guide tube and the applicator, characterized in that according to the invention, these drive means include:

a motor-driven roller capable of being put into tangential contact, with sliding, with the cable, means for causing the rotation of this motor-driven roller, and an encoder equipped with a roller capable of being put into tangential contact, without sliding, with the cable, this encoder being adapted for detecting an interruption in the rotation of this roller.

The words "device for driving and positioning at least one source holder in an applicator tube" are intended to mean that the invention applies to any number of applicator tubes. It can be used for placing a single source holder into an applicator, but typically, a plurality of applicators (on the order of 20) is used in radiotherapy. There is only a single source holder per applicator, and each source holder contains one or more sources.

Preferably the encoder used is an incremental encoder; that is, it emits a signal each time the roller is displaced by rotation about a given angle, that is, practically each time that the cable is displaced by a predetermined length.

Advantageously, a detector past which the source holder moves is mounted on the cable, in the course of the movement of the cable, can be provided, in order to count the sources. With this detector, it is possible not only to count the sources mounted on a given cable, but also to verify that the number of sources mounted on this cable is correct.

In another feature of the invention, the device further includes a first end-of-course detector in front of which the second end of the cable is located when the cable is in its first position.

Advantageously, the device may include a second end-of-course detector as well, located in such a manner as to detect the passage of the second end of the cable if the cable moves beyond the second position.

Finally, a second guide tube in which at least a portion of the cable can be displaced, can also be provided. This second guide tube has one end closed by a stop, and the second end of the cable comes into contact with this end, if the cable arrives on the near side of the first position.

The invention will become more apparent from the ensuing detailed description, which is given solely by way of illustrative example and in no way limits the scope of the invention, taken in conjunction with the accompanying drawings.

DESCRIPTION OF A PREFERRED EMBODIMENT

Figure 1:
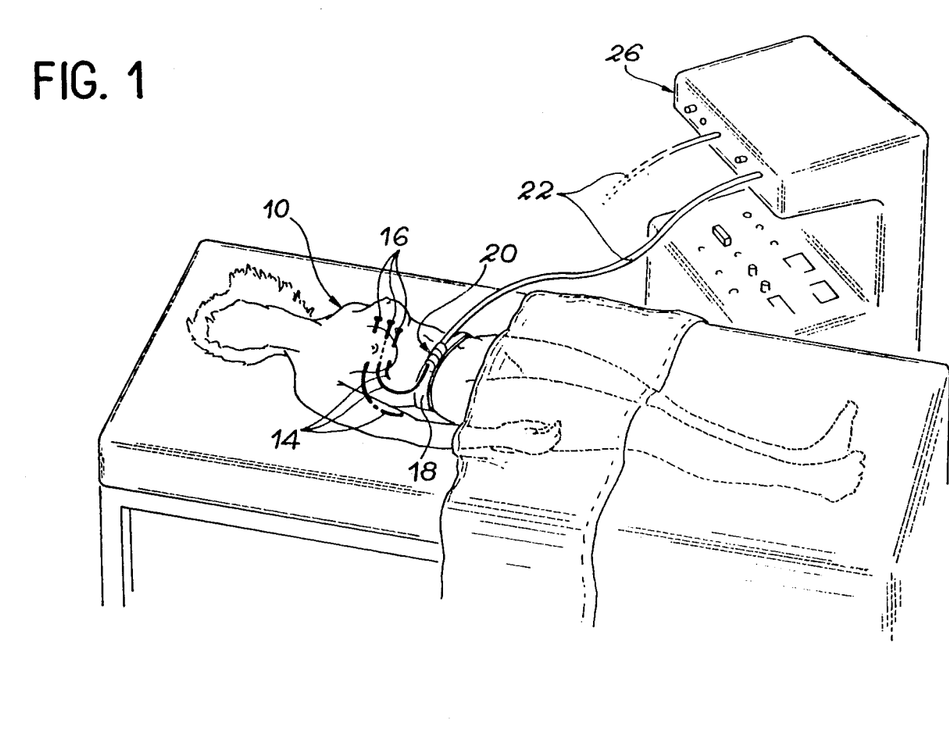
FIG. 1 is a schematic perspective view illustrating the general principle of radiotherapy.

In FIG. 1, a patient 10 suffering from breast cancer is shown lying on a treatment table 12. The treatment apparatus includes a certain number of applicators 14, which are tubes of small diameter at least a portion of which has been introduced into the interior of the diseased organ. Typically there are about 20 applicator tubes. The applicator tubes have a first end closed by a stop 16, while their other end is connected to a connection device 20 mounted on a belt 18 worn by the patient. A tube 22 of relatively large diameter has a connector 24 (FIG. 2) at one of its ends that enables it to be connected to the device 20, while its other end is connected to a machine 26 in which the devices for driving the cables on which the source holders are mounted is located.

The principle of radiotherapy treatment is as follows:

In a first period of time, the tube 22 is connected to the machine 26 and disconnected from the device 20. A certain number of cables, each placed in a guide tube, is located inside the tube 22, and their displacement is controlled by a device located inside the machine. The source holders intended for being placed inside the applicators 14 are located in a container (not shown in FIG. 1).

Figure 4:
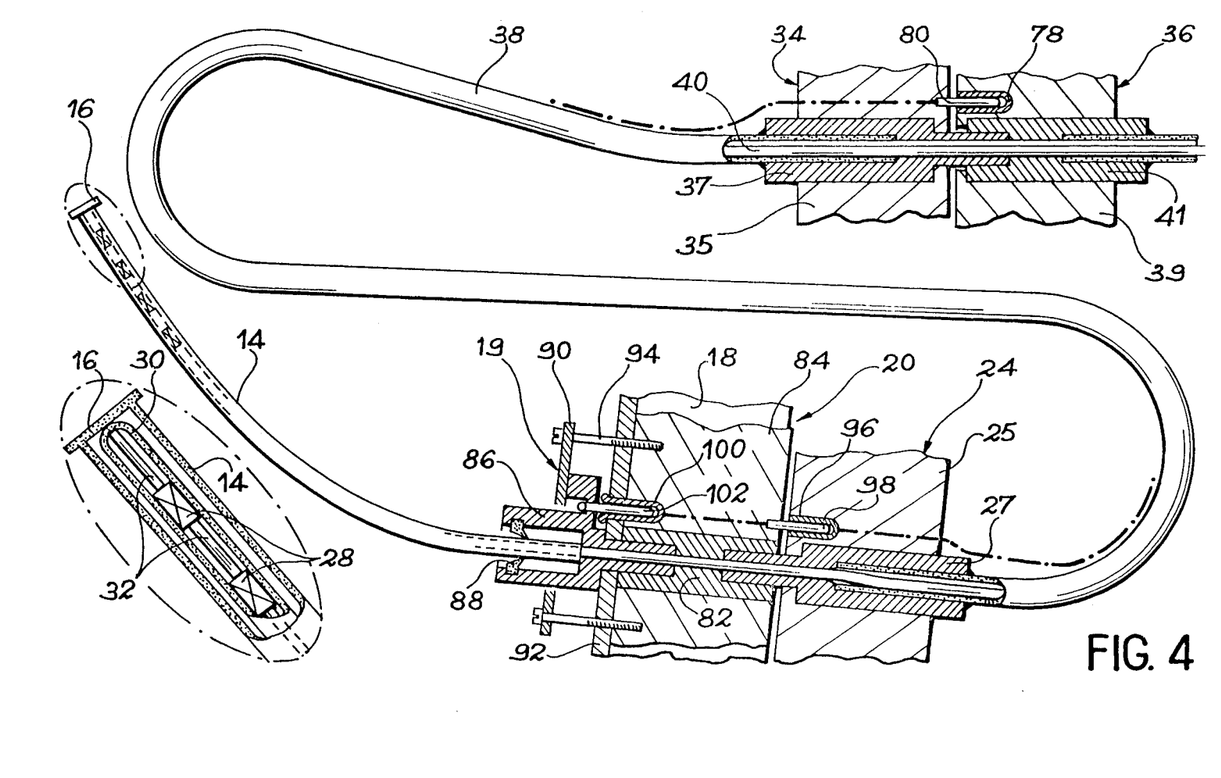
FIG. 4 is a schematic view, showing in section and in more detail the connections of the tube containing a plurality of guide tubes with the machine on the one hand and with the belt worn by the patient on the other.

One such source holder is shown on a larger scale in FIG. 4. In this drawing figure, the sources 28 are visible, placed one after the other inside the source holder tube 30. The sources are separated from one another by spacers 32. One such tube 30 is placed at the end of each of the cables that move inside guide tubes contained in the large-diameter tube 22.

Once the tubes 30 have initially been placed in a container, the tube 22 is first connected to the container, and the cables are maneuvered so that each of them is capable of finding a tube 30 in the container. The mounting of the tubes 30 on the cables is done with the aid of locking means, known per se and not described here. Next the cables are maneuvered along their guide tube, in order to put them in a position such that the sources will be placed inside a protective block, for example made of lead, provided inside the machine 26. The tube 22 is then disconnected from the container and connected to the device 20. Next, the cables are displaced in the reverse direction, until the tubes 30 arrive inside the applicators 14 and their ends are in contact with the stops 16 of these applicators.

Then the sources are allowed to act for the period of time necessary, which is on the order of one to two days. Once the treatment is completed, the cables are maneuvered once again in order to put them in their initial position, or storage position, in which the sources are located inside the lead block. The tube 22 is then disconnected from the device 20, and the applicators 14 are withdrawn.

It should be noted that the radioactive elements used in radiotherapy generally have short half-lives (for example, 74 days for iridium). As a consequence, the sources are not re-used for a second treatment; after use, they are sent to a radioactive waste storage and/or treatment facility.

Figure 2:
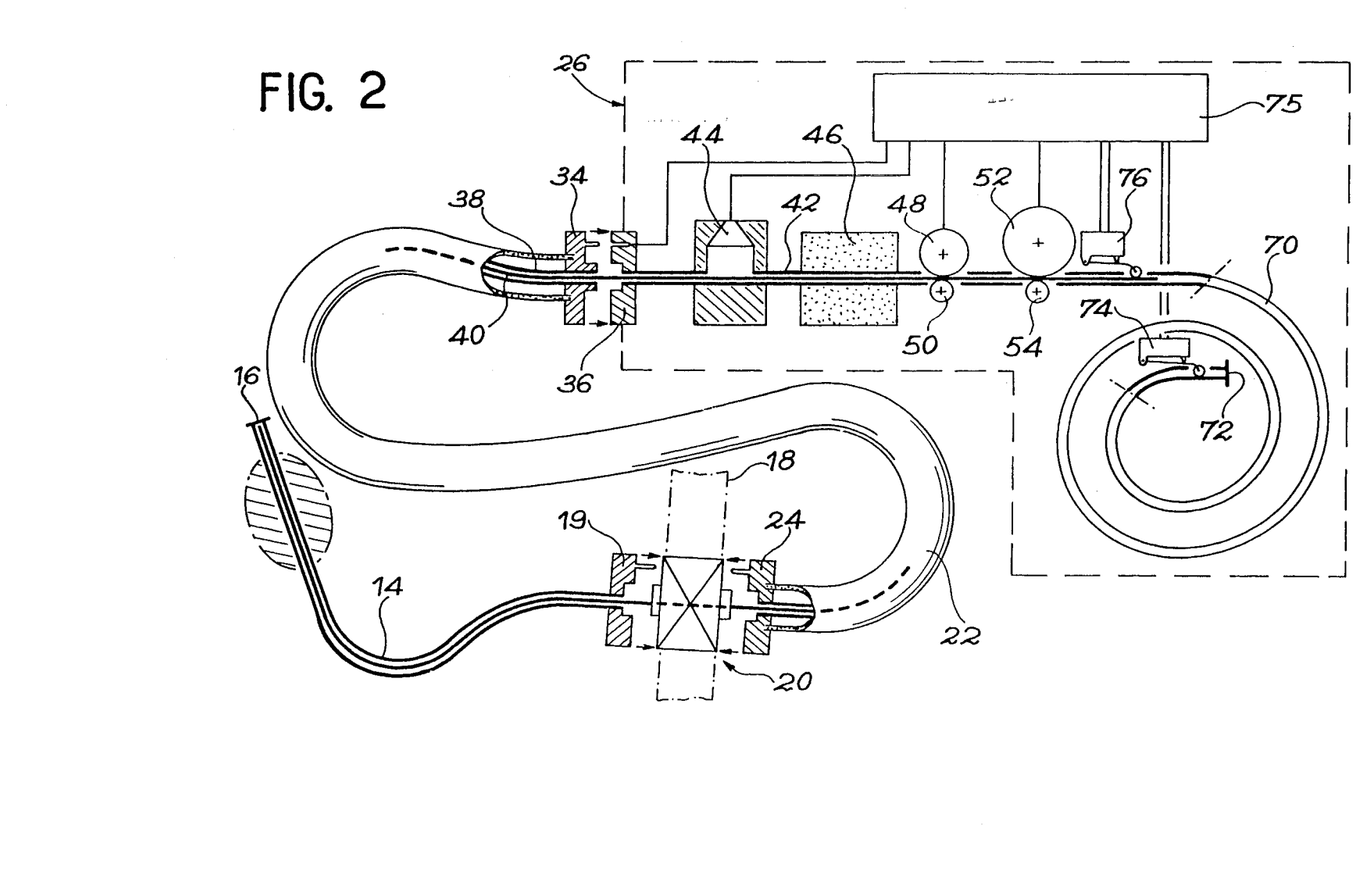
FIG. 2 is a schematic sectional view illustrating the main elements in the device according to the invention.

The sectional view of FIG. 2, in a more detailed fashion, shows the driving and positioning device according to the invention which enables the maneuvering of the cable on which the source holders are mounted. In this figure, the applicator tube 14 can be seen, which is connected to the device 20 of the belt 18 with the aid of a connector 19. The tube 22 is also visible, of which one end can be connected to the device 20 via a connector 24 and the other end can be connected to a connector 36 provided on one wall of the machine 26 via a connector 34. Also shown, inside the tube 22, is a guide tube 38 inside which the cable 40, with the source holder mounted at one end, can be displaced. In FIG. 2, only one applicator 14 and one cable 40 in its guide tube 38 are shown, but in reality there are a plurality of guide tubes 38 inside the tube 22, and a plurality of applicators. The connectors such as 19, 24, 34 and 36 are arranged for the passage of a plurality of cables 40, for example six cables.

FIG. 2 also shows a second guide tube 42 placed inside the machine, and inside which the cable 40 can be displaced. A detector 44 enables counting the number of sources located at the end of the cable 40 when the cable is put inside the machine 26. It should be noted that there are as many detectors 44 as cables 40. The role of these detectors is not only to count the sources located on a given source holder, but also to verify that the number of sources located on this source holder is indeed the intended number.

A block 46, which may a block of lead and through which the guide tube 42 passes, is always located inside the machine 26. The first position of the cable 40, or storage position, is the position in which the cable has entered the interior of the machine far enough that the sources are located inside this block. This assures protection and avoids radiation exposure to persons waiting for the connections to be made in order to be able to maneuver the cable 40 in the reverse direction in order to place the sources inside the applicator 40.

Also seen in FIG. 2 are the means for driving the cable 40 along the guide tubes 38 and 42. According to the invention, these drive means include a first roller or motor-driven roller 48 actuated by a motor not shown in FIG. 2. This roller 48 is in tangential contact with the cable, and it can slide slightly with respect to the cable. A counterpart roller 50 is provided opposite the roller 48. The drive means also include a second roller 52, which is also in tangential contact with the cable 40, but cannot slide with respect to the cable. A counterpart roller 54 is provided opposite the roller 52. The roller 52 is connected to an encoder, not shown in FIG. 2.

Figure 3:
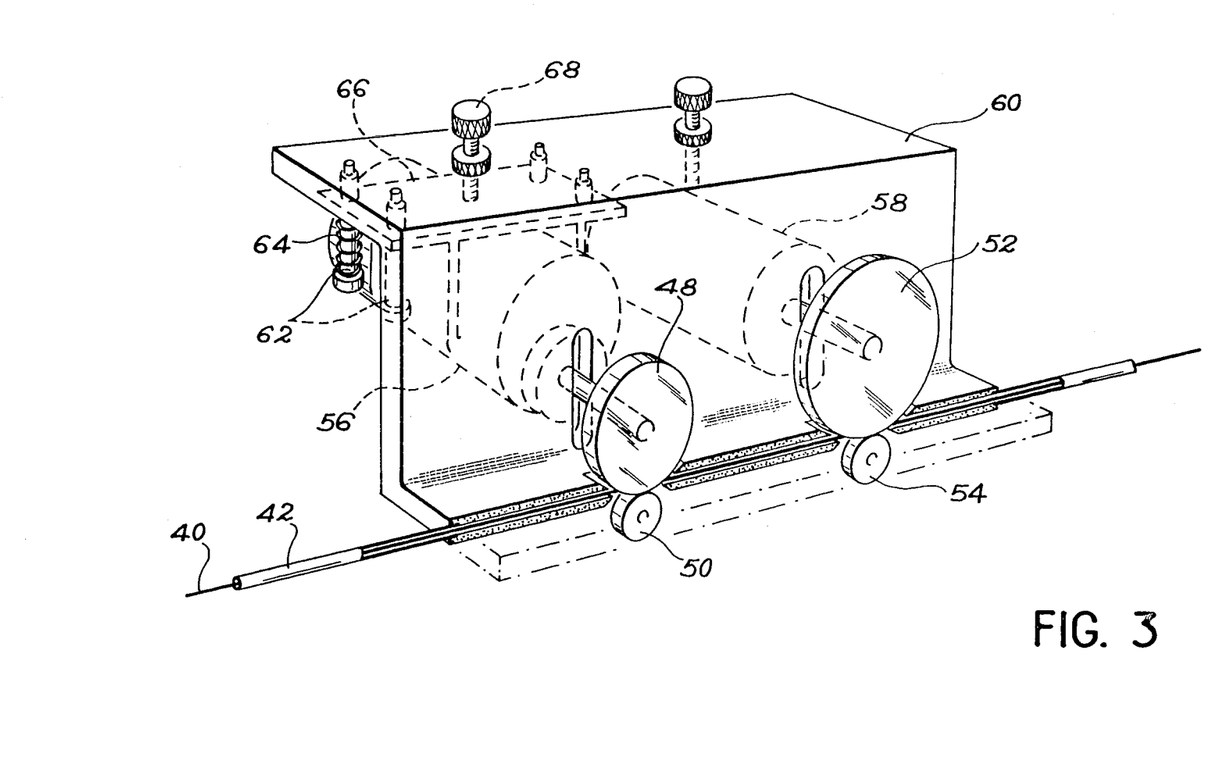
FIG. 3 is a schematic perspective view showing the motor driving the cable and the decoder on a larger scale.

The drive means are shown in greater detail in the perspective view of FIG. 3.

In this figure, it is seen that the motor 56 and the encoder 58 are mounted on a support 60. A device is provided for adjusting the height of the motor 56 and the encoder 58 and hence for regulating the force with which the rollers 48 and 52 are applied to the cable.

With suitable regulation of these forces of application, it is possible to proceed such that the roller 48 is in tangential contact, with sliding, with the cable 40 and the roller 52 is in tangential contact with the cable 40 without being able to slide with respect to it. To do so, four vertical guide columns 62 have been provided, mounted on the support 60. A spring 64 is located about each of the columns between the lower portion thereof and a plate 66, the position of which can be adjusted with the aid of a screw 68. The plate 66 is rigidly connected to the motor 56. It is the screw 68 that enables displacing the plate 66 counter to the action of the springs 64 and hence permits lowering the motor 56 to a variable extent and applying the roller 48 with variable force against the cable 40. A similar device is used for the encoder 58. It will be understood that in the exemplary embodiment shown here, the counterpart rollers 50 and 54 are fixed with respect to the support 60.

It will be understood that this is merely one example of a system capable of regulating the force of application of the roller 48 and 52 against the cable 40, and that an equivalent system can be used without departing from the scope of the invention. The essential feature is that the motor-driven roller 48 is capable of sliding with respect of the cable, and that the roller 52 cannot do so.

Returning once again to FIG. 2, it is seen that with respect to the cable 40 and to the guide tubes 38 or 42 containing it, the detectors 44 and the lead block 46 are located between the rollers 48 and 52 and the connector 36 that enables connection with the external tube 22.

Also shown in FIG. 2 is a third guide tube 70 placed on the opposite side of the detectors 44 and the block 46 with respect to the rollers 48 and 52. The length of the tube 70 is sufficient to permit the second end of the cable, that is, the end opposite the source holder, to be displaced when the cable is put in the storage position, in which the sources are located inside the block 46. The tube 70 is closed at its end opposite the rollers 48 and 52 by a stop 72. Also, two end-of-course detectors 74 and 76 are placed in proximity with the stop 72 and in the vicinity of the roller 52, respectively. Their displacement is such that the distance between these two detectors, counted along the guide tube 70, is slightly greater than the distance travelled by the cable when it moves from the storage position to the treatment position in which the source holder is in place in the applicator. The role of these two end-of-course detectors and of the stop 72 will be described later on in the present description.

Finally, a programmable control unit 75 provided inside the machine 26 makes it possible to control the entire apparatus, that is, essentially the detectors 44, the motor 56, the encoder 58 and the detectors 76 and 74.

The sectional view of FIG. 4 shows in further detail the connectors that enable connecting the tube 22 to the machine 26 and to the device 20 with which the belt 18 worn by the patient is equipped, as well as the connection system that enables the fixation of the applicators 14 on the device 20.

FIG. 4 shows that the connector 36 of the machine 26 comprises a plate 39 in which there are holes that can accommodate female plug sockets 41. In a similar manner, the connector 34 with which the end of the tube 22 on the side of the machine is equipped comprises a plate 35, in which openings have been made that enable accommodation of male plugs 37. Each of the male plugs 37 and female plug sockets 41 is pierced all the way through by a cylindrical duct enabling the passage of the guide tube 38 containing the cable 40.

The drawing also shows that a female plug socket 78 has been provided on the plate 39 and a male plug 80 mounted on the plate 35, in order to assure a continuous electrical supply to the unit.

At the other end of the tube 22 (not shown in FIG. 4), the connector 24 comprises a plate 25, in which a plurality of openings have been made to accommodate male plugs 27. Each male plug 27 is intended for being introduced into a connector piece 82, which in turn is mounted on a support 84 provided on the belt 18 worn by the patient. A male plug 86 is mounted on the end of the applicator 14 opposite the stop 16, or in other words on its end opposite that where the radioactive sources are located in the treatment position. A lip seal 88 assures tightness at the location where the applicator 14 penetrates to the interior of the plug 86. This plug 86 is provided for cooperation with the connector piece 82. The connector piece and the plugs 27 and 86 are provided with a central duct enabling the passage of the cable 40.

A locking plate 90 which is fixed on a retention plate 92 with the aid of screws 94 assures that the plugs 86 will be held in position. The plate 25 is provided with a female plug socket 96 that can cooperate with a male plug 98 carried by the support 84. Similarly, on the side of the applicator 14, the applicator is provided with a female plug socket 100 capable of cooperating with a male plug 102 mounted on the plate 90. The plates such as 39, 35 or 25 can be provided with any arbitrary number of openings, for example 10, and thus permit the simultaneous connection of an equal number of guide tubes. The connection device 20 has as many connector pieces, such as 82, as there are plugs 27 and plugs 86 to be connected.

Figure 5:
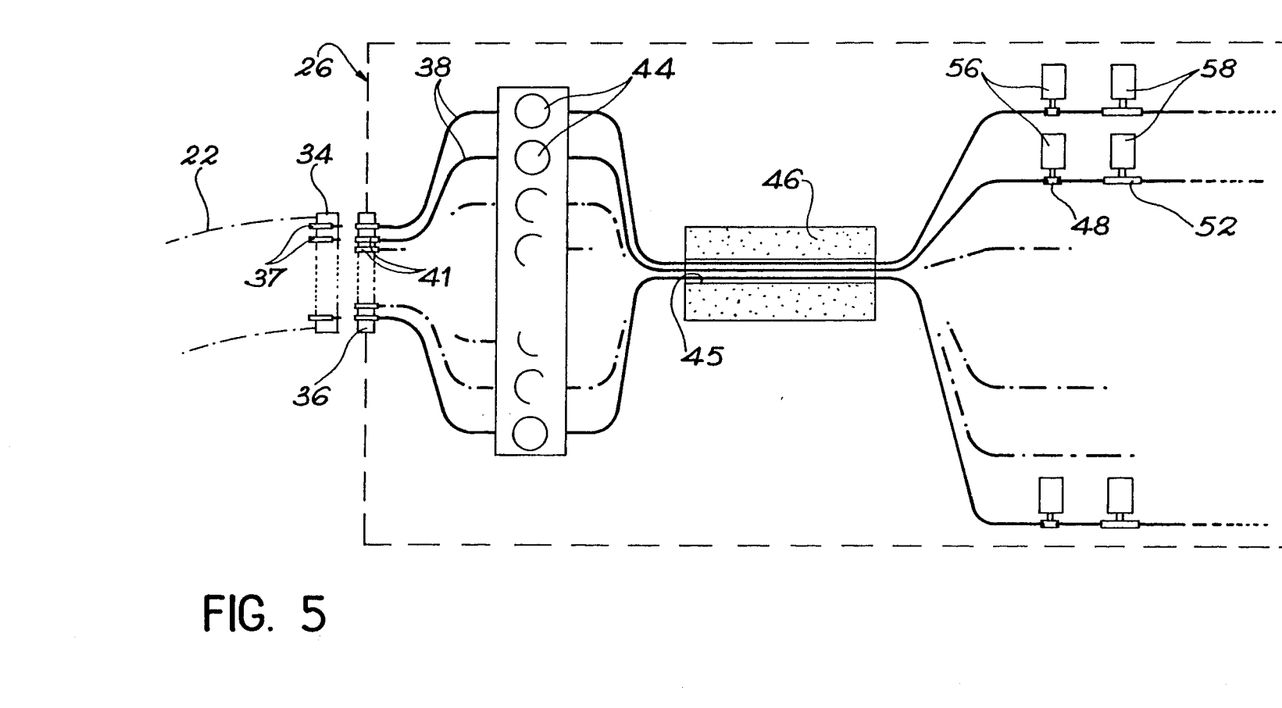
FIG. 5 is a schematic view showing how a plurality of devices according to the invention can be disposed inside one machine.

The schematic view of FIG. 5 shows how a plurality of driving devices according to the invention can be installed inside a given machine.

In the particular case described here, a group of 10 driving devices has been shown, but two groups each including six similar devices can be provided in a single machine. It will be understood that a change in the number of groups and/or devices in a given group does not depart from the scope of the invention. In this figure, the connectors 34 are seen, mounted on the end of the tube 22 and 36 which is mounted on one wall of the machine. A plurality of guide tubes 38 (in the example shown, 10) originate at the connector 36 and each of them extends past a detector 44. All of the guide tubes then move into the central duct 45 of the lead block 46. It should be noted that although it is necessary to have a detector 44 for each tube 38 in order to count the sources located in a given source holder, it is not necessary to have as many protection blocks 46 as there are tubes 38. The construction is simplified and the weight of the machine is reduced if only a single block is used, provided with a duct sufficiently large to enable the passage of the all the guide tubes. On the opposite side of the block 46 from the detector 44, the bundle of guide tubes separates once again, so that each cable can pass before a motor 56 and an encoder 58. It will be understood from the foregoing description that the rollers with which a motor and an encoder are respectively equipped will act upon only a single cable each, and that as many motor-encoder sets like that shown in FIG. 3 are needed as there are cables. Similarly, there are as many guide tubes 70, such as that shown in FIG. 2, and optionally detectors 74 and 76 mounted on such a guide tube, as there are cables inside the machine.

The function of the drive device according to the invention is as follows:

The motor-driven roller 48 mounted on the motor 56 drives the cable when the motor is subjected to voltage. This enables advancing the cable along the guide tubes, such as 40 and 42, and placing the cable at all the desired positions; that is, the locking position of the source holder located inside a container, the storage position in which the source holders are placed inside the machine, inside the block 46, and the treatment position in which the source holders are located inside the applicator 14. The roller 52 with which the encoder is equipped is in tangential contact, without sliding, with the cable 40. This means that when the cable is in motion, the roller 52 is driven to rotate. If the cable encounters an obstacle along its way, it immediately stops. Since the roller 52 cannot slide with respect to the cable, its rotation stops equally quickly. Meanwhile, since the motor-driven roller 48 can slide with respect to the cable, it continues to rotate. Since the encoder 58 is capable of sending signals as a function of the angular position of the roller 52, the length of cable that has unwound from a predetermined original position when the rotation of the roller 52 is interrupted can be detected. It is thus possible to know whether the obstacle encountered by the cable is the stop 16 located at the end of the applicator 14, or a hindering obstacle located along the way. Thus, knowing the length of cable that has unwound, it is possible to determine with good precision the site of the obstacle encountered by the end of the cable.

In the preferred embodiment, the encoder 58 is an incremental encoder; that is, it sends a signal each time the roller 52 has rotated by a predetermined angle or in other words, each time that the cable is displaced by a given length. If the cable 40 ceases its displacement, the encoder stops sending signals, and this state is detected by the programmable control unit 75, which confirms that the roller 58 is no longer rotating. Since the roller 48 is capable of sliding with respect to the cable, it continues to rotate. The programmable control unit then directs the stoppage of the motor. On the other hand, if the obstacle encountered is not the stop 16 located at the end of the applicator 14, the control unit commands the return of the source holder into the block 46, to prevent radiation exposure to personnel. The same source holder can then be re-injected into its guide tube, because it may happen that there was not in fact any obstacle and that the source holder or cable was blocked against the inside wall of the guide tube, for example. If the device again detects an obstacle, an operator will intervene in order to eliminate it.

If the length of the cable that has been unwound from a given original position up to the interruption of rotation of the roller 52 corresponds to a position in which the source holder tube 30 is at the end of the applicator 14, then it is known that the obstacle is none other than the stop 16 located at the end of the applicator, and it is certain that the radioactive sources are in the proper position inside the applicator.

It should be noted that the cable can undulate somewhat, and that the length of cable that has travelled past the roller 52 is slightly greater than the distance actually travelled by the source holder. Preliminary tests will enable determining the length of cable corresponding to the position in which the source holder is in contact with the stop 16.

Safety devices are provided for stopping the unwinding of the cable in one direction or the other in order that the displacement of the cable will remain within predetermined limits. It may for example happen that the stop 16 is missing at the end of the applicator 14. For this purpose, the end-of-course detector 76 has been provided. This detector is placed on the opposite side of the applicator 14, with respect to the rollers 48 and 52. Moreover, its placement is such that if the anterior end, or first end, of the cable, that is, the end carrying the radioactive sources, exits from the applicator 14 in case of the accidental absence of the stop 16, the second end or posterior end of the cable will travel past the detector 76 after a very short period of time has elapsed. This detector can then send a signal to the control unit 75, and the control unit will command the stoppage of the motor 48 and possibly the emission of an alarm signal. It should be noted that the detector 76 does not intervene except in this case, and that if the anterior end of the cable, or more specifically the anterior end of the source holder tube comes into contact with the stop 16, the other end of the cable will not yet have travelled past the detector 76.

Similarly, safety devices have provided for the reverse movement of the cable, that is, to assure the stoppage of the cable when the sources are placed inside the machine 26, so that they will not move beyond the block 46. It is in fact necessary to stop the motion of the cable at this level in order that the sources remain inside the protection block. This is why the detector 74 is provided. Thus once the cable 40 has been placed inside the machine, this movement continues until the posterior end of the cable travels past the detector 74. At that instant, this detector sends a signal to the programmable control unit 75, and the control unit commands the stoppage of the motor 56. The position of the detector 74 is such that the posterior end of the cable travels past it when the source holder tube is located entirely inside the block 46.

Finally, in case of a malfunction of the detector 74, a stop 72 has been provided at the corresponding end of the guide tube 70. Thus if the posterior end of the cable travels past the detector 74 without this detector emitting a signal controlling the stoppage of the motor, the movement will continue, but the end of the cable will be blocked by the stop 72. Since the cable will then be abruptly immobilized, the roller 52 of the encoder will in turn be immobilized immediately, and the encoder will send an identical signal to that sent when the cable encounters an obstacle. Since the system is programmed, and the length of cable that has been unwound is known, it will be known that this stoppage is due to the fact that the posterior end of the cable has come into contact with the stop 72. As noted above, it may happen that here again the cable has undulated somewhat, and preliminary tests will make it possible to determine the position of the cable so that its second end is in contact with the stop 72.

The driving and positioning device that is the subject of the invention has numerous advantages, since it makes it possible to know the position of the cable at any instant, to detect the presence of an obstacle, and to determine with precision the location of the obstacle. It also makes it possible to assure the correct positioning of the sources in the applicator tube. Moreover, safety devices are provided for stopping the movement of the cable in one direction or the other in the case of problems, for example in the event that the stop 16 at the end of the applicators 14 is absent, or in case of malfunction of the end-of-course detector 74.

Finally, given that the cable may undergo some undulation, simply measuring the length of cable that has unwound is not enough to assure that the source holder is in proper position in the applicator. The device according to the invention enables assuring that the source is indeed in place in the applicator, because the unwinding of the cable does not stop except in the event of an obstacle; if this obstacle is the stop 16, then the control unit does not command the return of the cable, and it is known with certainty that the source holder is properly positioned.

It should also be noted that the cable is changed for each treatment, because the sources are retracted each time the staff enters the treatment station, to prevent radiation exposure. The movements of the cables can be controlled from outside this station. Hence, in the course of one treatment, each cable may make approximately 50 trips back and forth. The cable is then fragile, and the probability of encountering an obstacle is increased; this necessitates detecting any obstacles with certainty, and the device according to the invention makes this possible.

Finally, it is understood that the invention is not limited to the single embodiment described above, but that variants are also possible without departing from the scope of the invention. One skilled in the art will be able to vary the number and emplacement of guide tubes, such as 40, 42 and 70, in which the cable 40 moves. Other connection systems than the connectors 34, 36 or the device 20 can be used, or optionally they can be omitted, if the structure of the apparatus makes it possible to dispense with such connections. Any kind of detector can be used for counting the sources, or these devices can be optionally omitted. Similarly, the safety devices, such as the end-of-course detectors 74 and 75 and the stop 72, are not obligatory and can optionally be replaced with other systems. The stop 16 located at the end of the applicator 14 can be omitted and replaced with a different stop placed along the path of the cable. The cable will then be equipped with some element that comes into contact with this other stop when the sources are properly placed inside the applicator. Finally, although only a single cable 40 has been taken into account in the above description, it will be understood that a plurality of devices according to the invention can be placed in a given machine. In that case there will be as many motors 56 and encoders 58 equipped with rollers 48 and 52 as there are cables to be maneuvered.

What is claimed is:

1. A device for driving and positioning at least one radioactive source holder in an applicator tube used in radiotherapy, the applicator tube having a first end and a second end, the second end being open, said device comprising:
    a guide tube having one end connected to said second end of the applicator tube,
    a cable longitudinally displaceable along said guide tube and said applicator tube between a first position and a second position, the cable having a first end in the vicinity of which said source holder is mounted, and second end, and
    means for driving the cable along the guide tube and the applicator tube,
    the driving means including:
        a motor-driven first roller in tangential contact, with sliding, with the cable,
    means for causing rotation of the motor-driven first roller, and
    an encoder equipped with a second roller in tangential contact, without sliding, with the cable, the encoder having means for detecting an interruption in the rotation of the second roller.

2. A device as defined by claim 1, wherein the encoder is an incremental encoder.

3. A device as defined by claim 1, further including a detector past which the source holder moves when it is mounted on the cable, in the course of displacement of the cable, for counting sources.

4. A device as defined by claim 1, further including a first end-of-course detector in front of which the second end of the cable is located when the cable is in its first position.

5. A device as defined by claim 1, further including a second end-of-course detector located in such a manner as to detect the passage of the second end of the cable if the cable moves beyond said second position.

6. A device as defined by claim 1, further including a second guide tube in which at least a portion of the cable can be displaced, the second guide tube having one end closed by a stop, the second end of the cable coming into contact with the stop upon the cable being displaced to near said first position.

7. A device for driving and positioning a radioactive source holder in an applicator tube used in radiotherapy, the applicator tube having a first end and an open second end, said device comprising:
   a guide tube having one end connected to the second end of the applicator tube;
   a cable displaceable longitudinally along the guide tube and the applicator tube between a first position and a second position, the cable having a first end and a second end and the source holder being mounted on the cable in the vicinity of the first end;
   means for driving the cable along the guide tube and the applicator tube including a first drive roller in tangential and sliding contact with the cable, and means for rotating the first roller to drive the cable;
   an encoder having a second roller in tangential non-sliding contact with the cable and having means for detecting an interruption in the rotation of the second roller; and
   an end-of-course detector in front of which the second end of the cable is located when the cable is in the first position.

8. A device for driving and positioning a radioactive source holder in an applicator tube used in radiotherapy, the applicator tube having a first end and an open second end, said device comprising:
   a guide tube having one end connected to the second end of the applicator tube;
   a cable displaceable longitudinally along the guide tube and the applicator tube between a first position and a second position, the cable having a first end and a second end and the source holder being mounted on the cable in the vicinity of the first end;
   means for driving the cable along the guide tube and the applicator tube including a first drive roller in tangential and sliding contact with the cable, and means for rotating the first roller to drive the cable;
   an encoder having a second roller in tangential non-sliding contact with the cable and having means for detecting an interruption in the rotation of the second roller; and
   an end-of-course detector located to detect passage of the second end of the cable upon the cable moving beyond said second position.

* * * * *

UNITED STATES PATENT AND TRADEMARK OFFICE
CERTIFICATE OF CORRECTION

PATENT NO. : 4,851,694

DATED : July 25, 1989

INVENTOR(S) : RAGUE et al

It is certified that error appears in the above-identified patent and that said Letters Patent is hereby corrected as shown below:

On the cover page, in the block for the assignee, please change "Campaignie ORIS Industrie" to -- COMPAGNIE ORIS INDUSTRIE --.

Signed and Sealed this

Fifth Day of March, 1991

Attest:

HARRY F. MANBECK, JR.

*Attesting Officer*    *Commissioner of Patents and Trademarks*